US009266140B2

(12) United States Patent
Gunsell et al.

(10) Patent No.: US 9,266,140 B2
(45) Date of Patent: Feb. 23, 2016

(54) ANNULAR ADHESIVE BEAD APPLICATION

(71) Applicant: Lockheed Martin Corporation, Bethesda, MD (US)

(72) Inventors: Timothy Mathew Gunsell, Fort Worth, TX (US); Daniel Dario Lopez, Fort Worth, TX (US); Dan E. Hartzell, Fort Worth, TX (US); Richard A. Luepke, Forth Worth, TX (US)

(73) Assignee: Lockheed Martin Corporation, Bethesda, MD (US)

( * ) Notice: Subject to any disclaimer, the term of this patent is extended or adjusted under 35 U.S.C. 154(b) by 533 days.

(21) Appl. No.: 13/683,470

(22) Filed: Nov. 21, 2012

(65) Prior Publication Data

US 2014/0138413 A1 May 22, 2014

(51) Int. Cl.

| | |
|---|---|
| ***B67D 1/07*** | (2006.01) |
| ***B65D 25/42*** | (2006.01) |
| ***B05C 17/00*** | (2006.01) |
| ***A61B 17/00*** | (2006.01) |
| ***B05C 5/02*** | (2006.01) |
| ***B65D 83/00*** | (2006.01) |
| ***B65D 47/08*** | (2006.01) |
| ***B05C 17/005*** | (2006.01) |
| ***B05B 1/06*** | (2006.01) |
| ***B05C 17/01*** | (2006.01) |

(52) U.S. Cl.

CPC ................. *B05C 5/0241* (2013.01); *B05B 1/06* (2013.01); *B05C 17/00* (2013.01); *B05C 17/002* (2013.01); *B05C 17/00516* (2013.01); *B05C 17/01* (2013.01); *B65D 47/08* (2013.01); *B65D 83/00* (2013.01)

(58) Field of Classification Search

CPC ................................ B05B 1/00; F16B 11/006

USPC ................ 401/9–11, 143; 222/566, 568, 327; 413/60, 18; 118/711; 411/258, 82–85

See application file for complete search history.

(56) References Cited

U.S. PATENT DOCUMENTS 4,385,728 A 5/1983 Inglis et al.
4,429,658 A 2/1984 Jones (Continued)

FOREIGN PATENT DOCUMENTS

FR 2606674 A1 5/1988

(Continued)

OTHER PUBLICATIONS

Extended European Search Report dated May 9, 2014 for Application No. 13193709.6-1760, 5 pages.

*Primary Examiner* — David Walczak
*Assistant Examiner* — Thomas M Abebe
(74) *Attorney, Agent, or Firm* — Reising Ethington P.C.

(57) ABSTRACT

Application of uncured adhesive material in bead ring on a surface using a device that includes a nozzle comprising a nozzle intake port, a nozzle outlet port, and a nozzle cavity connecting and providing fluid communication between the inlet and outlet ports. The nozzle intake port receives uncured adhesive material into the nozzle cavity from a source of uncured adhesive material. The outlet port has an annular shape that forms an annular bead of adhesive material on a surface onto which the nozzle is dispensing adhesive material. The nozzle cavity comprises an annular flow path leading to the annular outlet port and shaped to dispense adhesive material through the outlet port axially. The nozzle comprises inner and outer concentric walls defining the annular flow path therebetween.

17 Claims, 3 Drawing Sheets

(56) References Cited

U.S. PATENT DOCUMENTS

| | | | | |
|---|---|---|---|---|
| 4,842,469 | A * | 6/1989 | Schmidt | 413/60 |
| 5,605,541 | A | 2/1997 | Holm | |
| 7,845,536 | B2 | 12/2010 | Viola et al. | |
| 2005/0051571 | A1 * | 3/2005 | Carruth et al. | 222/1 |
| 2012/0217673 | A1 * | 8/2012 | Hutter, III | 264/219 |

FOREIGN PATENT DOCUMENTS

| | | | |
|---|---|---|---|
| GB | 1042714 | | 9/1966 |
| GB | 1399924 | A | 7/1975 |
| GB | 2470486 | A | 11/2010 |
| GB | 2470488 | A * | 11/2010 |
| WO | 8301747 | A1 | 5/1983 |

* cited by examiner

ANNULAR ADHESIVE BEAD APPLICATION

CROSS-REFERENCES TO RELATED APPLICATIONS

Not Applicable

STATEMENT REGARDING FEDERALLY SPONSORED RESEARCH OR DEVELOPMENT

Not Applicable

BACKGROUND

1. Field

This application relates generally to a method and device for applying an annular bead of adhesive material to a surface.

2. Description of Related Art Including Information Disclosed Under 37 CFR 1.97 and 1.98

Manufacturing processes in many fields require large numbers of extremely precise and consistent applications of adhesive material. For example, the preparation of thousands of holes commonly formed in aircraft skin panels to receive skin panel fasteners includes the mounting of thousands of nutplates in alignment with the respective skin panel fastener holes. To affix each nutplate, it is known to apply an annular bead of adhesive material either to a flange portion of the nutplate around a fastener hole in the nutplate, or to a skin panel to which the nutplate is to be affixed, around a corresponding skin panel fastener hole. The nutplate is then applied to the skin panel with the nutplate fastener hole aligned with the skin panel fastener hole and the annular bead of adhesive material sandwiched between the nutplate flange and the skin panel. In either case, the annular bead of adhesive material must be applied consistently in sufficient quantity and with sufficient surface area to securely attach the nutplate to the skin panel without flowing into and migrating along the nutplate fastener hole and between the flange and a floating element of the nutplate. Curing of adhesive material between a flange and floating element of a nutplate can jam or otherwise impede proper functioning of the nutplate. Current adhesive material application techniques rely on installer skill to accomplish the task of adhesive material application, with the inevitable result being that many nutplates are either insufficiently attached (resulting in failure of a subsequent push test, and requiring reinstallation), or are rendered inoperable due to adhesive contamination and must be replaced.

SUMMARY

An adhesive applicator device is provided for applying uncured adhesive material in a bead ring to a surface. The device includes a nozzle comprising a nozzle intake port, a nozzle outlet port, and a nozzle cavity connecting and providing fluid communication between the inlet and outlet ports. The nozzle intake port is configured to receive uncured adhesive material into the nozzle cavity from a source of uncured adhesive material. The outlet port has an annular shape configured to form an annular bead of adhesive material on a surface onto which the nozzle is dispensing adhesive material. The nozzle cavity comprises an annular flow path that leads to the annular outlet port and is shaped to dispense adhesive material axially through the outlet port. The nozzle also comprises inner and outer concentric walls that at least partially define the annular flow path therebetween. The inner concentric wall of the applicator nozzle extends axially beyond the outer concentric wall to allow outward radial movement of uncured adhesive material and to block inward radial encroachment of uncured adhesive material.

Also provided is an adhesive applicator device that includes a nozzle comprising a nozzle intake port, a nozzle outlet port, and a nozzle cavity connecting and providing fluid communication between the inlet and outlet ports; the nozzle intake port being configured to receive uncured adhesive material into the nozzle cavity from a source of uncured adhesive material, the outlet port having an annular shape configured to form an annular bead of adhesive material on a surface onto which the nozzle is dispensing adhesive material, the nozzle cavity comprising an annular flow path that leads to the annular outlet port and is shaped to dispense adhesive material axially through the outlet port, and nozzle comprising inner and outer concentric walls that at least partially define the annular flow path therebetween, and the inner and outer concentric walls being shaped and positioned such that the annular flow path tapers in cross-sectional area in a flow direction of adhesive material along the annular flow path.

DRAWING DESCRIPTIONS

These and other features and advantages will become apparent to those skilled in the art in connection with the following detailed description and drawings of one or more embodiments of the invention, in which.

Figure 2:
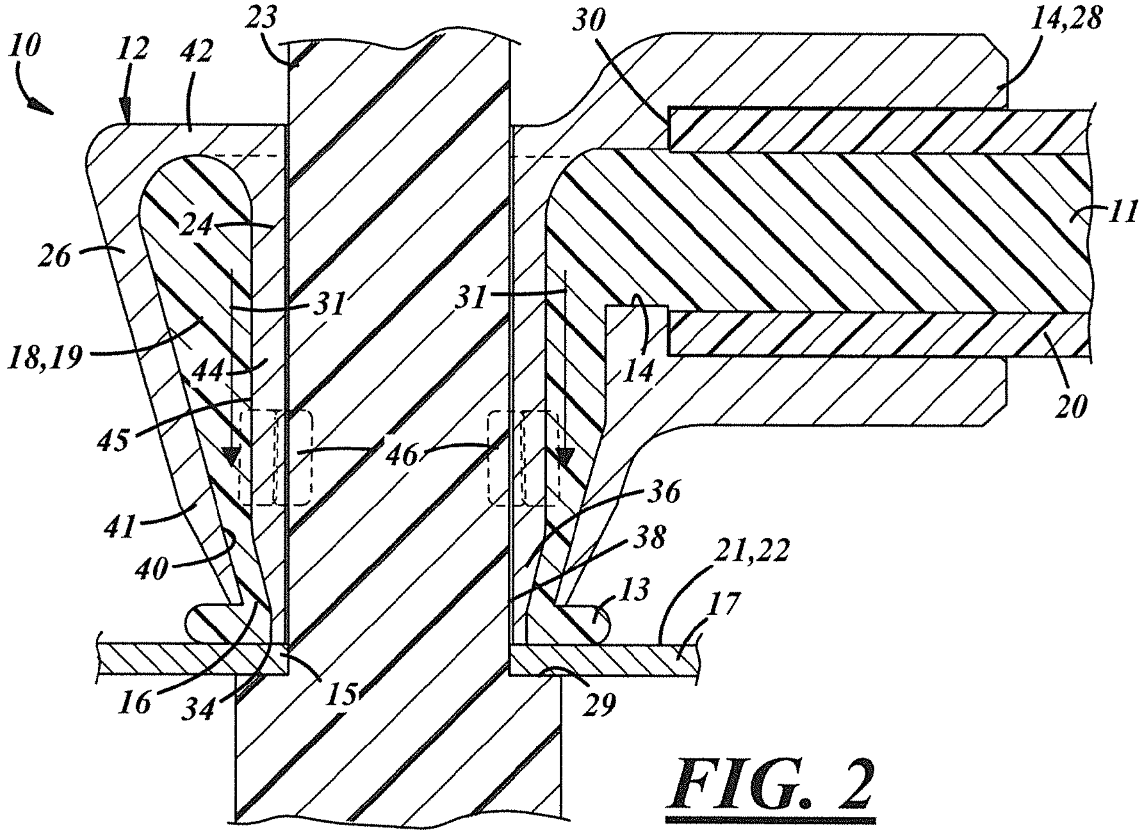
FIG. 2 is a fragmentary cross-sectional side view of the adhesive applicator device and dispenser gun of FIG. 1 being held in coaxial alignment with a fastener hole of a nutplate by a nutplate positioning worm while applying adhesive material to a flange of the nutplate.
Figure 7:
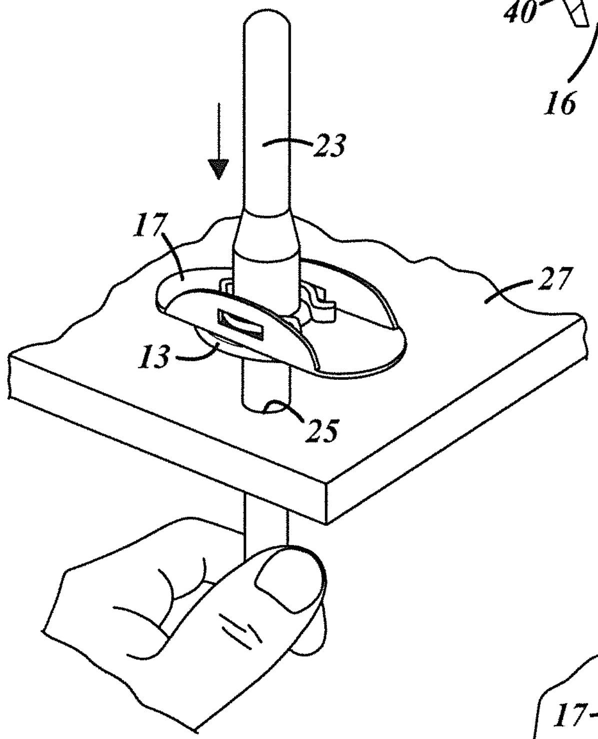
Figure 8:
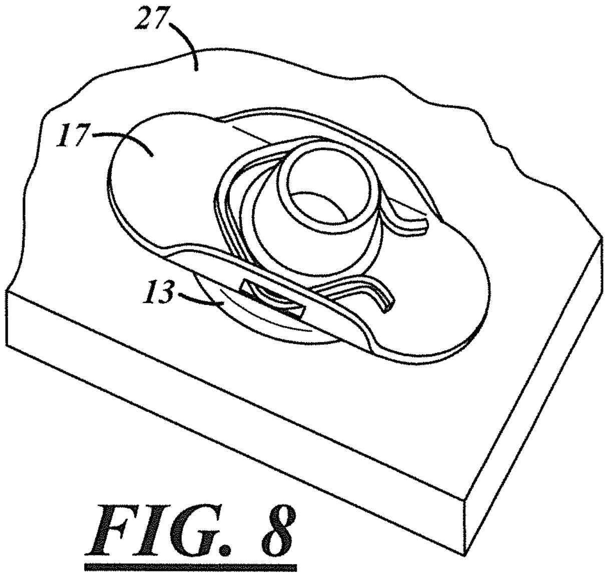

FIG. 7 is an orthogonal view of the nutplate of FIG. 2 with adhesive material having been applied and with the nutplate and adhesive material being supported and drawn against a panel in alignment with a panel fastener hole by the nutplate positioning worm of FIG. 2; and FIG. 8 is an orthogonal view of the nutplate of FIG. 7 affixed to the panel of FIG. 7 with the nutplate positioning worm of FIG. 7 having been removed.

DETAILED DESCRIPTION

An adhesive applicator device for applying uncured adhesive material 11 in a bead ring 13 surrounding a fastener hole 15 in a nutplate 17 is generally shown at 10 in FIGS. 1-6. As best shown in FIG. 2, the device 10 may comprise a nozzle 12, with the nozzle 12 comprising a nozzle intake port 14, a nozzle outlet port 16, and a nozzle cavity 18 connecting and providing fluid communication between the intake 14 and outlet ports 16. The nozzle intake port 14 may be configured to receive uncured adhesive material 11 into the nozzle cavity

18 from a source 20 of uncured adhesive material 11. The outlet port 16 may have an annular shape configured to form an annular bead ring 13 of adhesive material 11 on a surface 22 onto which the nozzle 12 is dispensing adhesive material 11. The nozzle cavity 18 may comprise an annular flow path leading to the annular outlet port 16 and shaped to dispense adhesive material 11 axially through the outlet port 16. The nozzle 12 may also comprise inner and outer concentric walls 24, 26 that may at least partially define the cavity 18 and the annular flow path therebetween. The inner concentric wall 24 of the applicator nozzle 12 may protrude or extend axially beyond the outer concentric wall 26 to allow outward radial movement of uncured adhesive material 11 and to block inward radial encroachment of uncured adhesive material 11.

Figure 1:
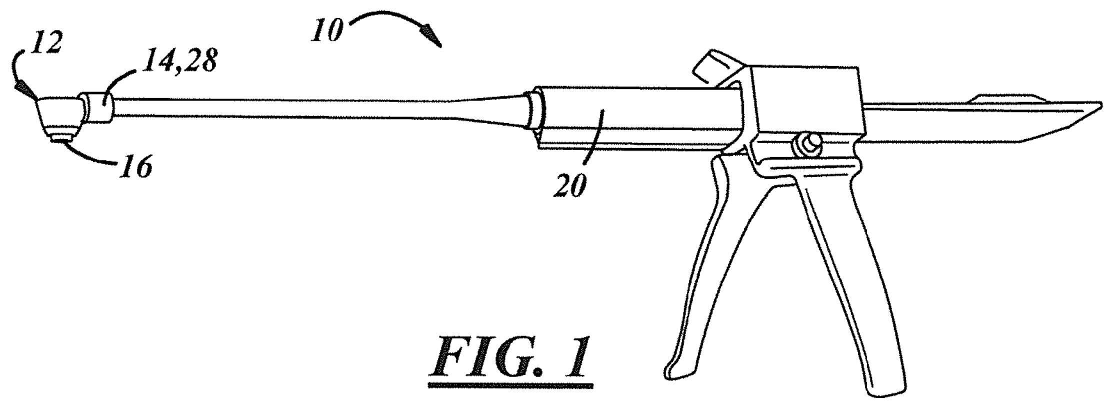
FIG. 1 is a perspective view of an adhesive applicator device carried by an adhesive dispenser gun.

As shown in FIG. 1, the nozzle intake port 14 may be configured to receive the adhesive material 11 from the source 20 of uncured adhesive material, for example, an adhesive dispenser gun. The intake port 14, best shown in FIG. 2, may be established by an intake fitting 28, which may be carried by the nozzle 12, through which the adhesive material 11 from the gun 20 may be received into the nozzle cavity 18. The intake fitting 28 may be configured to receive a mixing tip 30 of the adhesive dispenser gun 20 and to guide the adhesive material 11 from the mixing tip 30 of such a dispenser gun 20 into the annular flow path of the nozzle cavity 18 through the nozzle intake port 14. The intake fitting 28 may be oriented such that the uncured adhesive material 11 is received into the nozzle cavity 18 in a radially inward direction generally perpendicular to the annular flow path. To ensure consistent adhesive material flow, the dispenser gun 20 may be a precision sealant dispensing system (PSDS) having pulsed volume control and configured such that a single trigger pull of the adhesive dispenser gun 20 will deliver an amount of uncured adhesive material 11 equal to a desired annular adhesive material bead volume.

Figure 4:
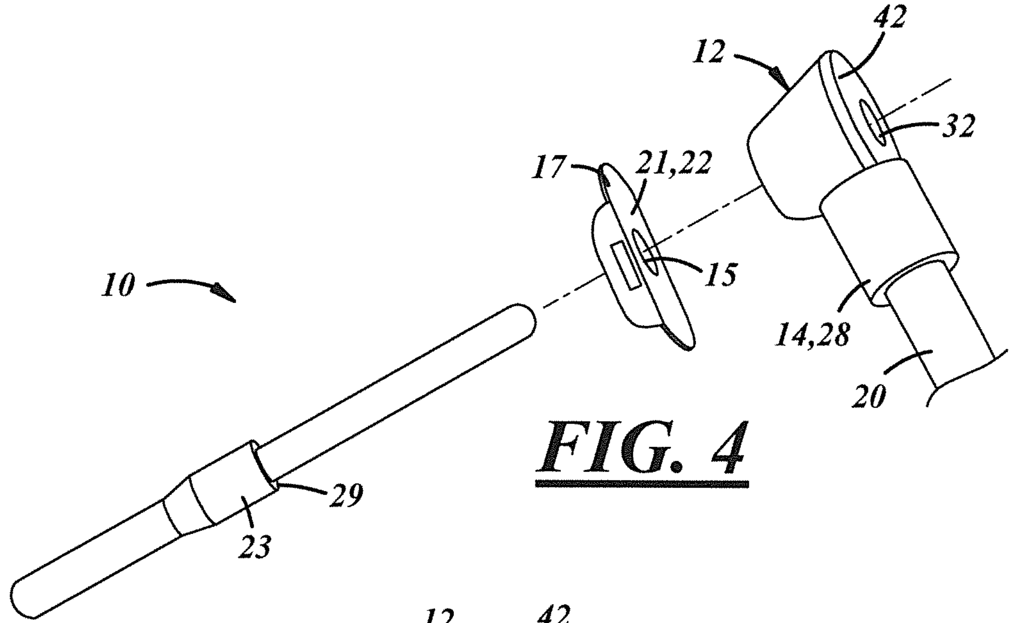
FIG. 4 is a fragmentary exploded perspective view of the adhesive applicator device, dispenser gun barrel, nutplate, and nutplate alignment worm of FIG. 2.
Figure 5:
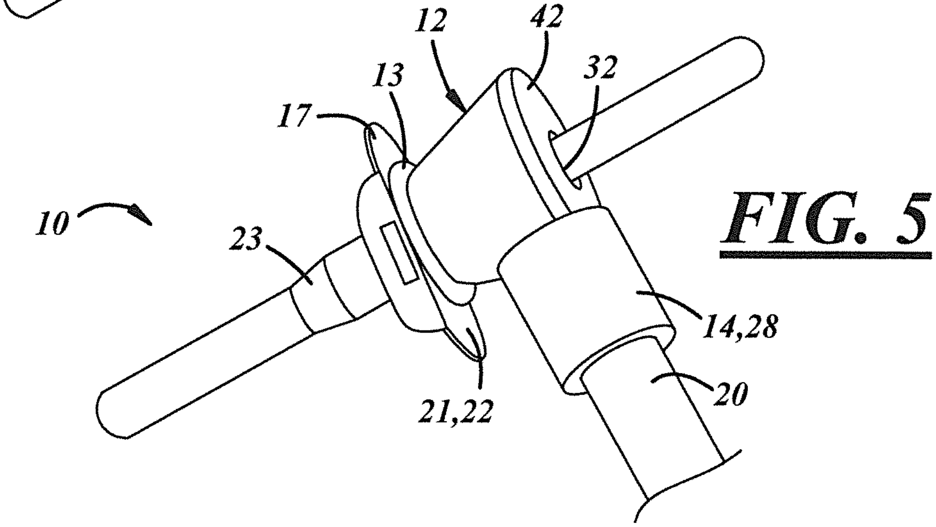
FIG. 5 is an enlarged perspective fragmentary view of the adhesive applicator device, dispenser gun barrel, nutplate, and nutplate alignment worm of FIG. 4 showing the adhesive applicator device applying a bead of adhesive material to a flange portion of the nutplate while being held in alignment by the nutplate alignment worm.

As shown in FIGS. 2, 4, and 5, the device 10 may be configured to apply the uncured adhesive material 11 in the bead ring 13 to a surface of a flange portion 21 of a nutplate 17 surrounding the fastener hole 15 of the nutplate 17. The nutplate 17 may be of any suitable type including, but not limited to, a type available from Click Bond, Inc. of Carson City, Nev.

Figure 3:
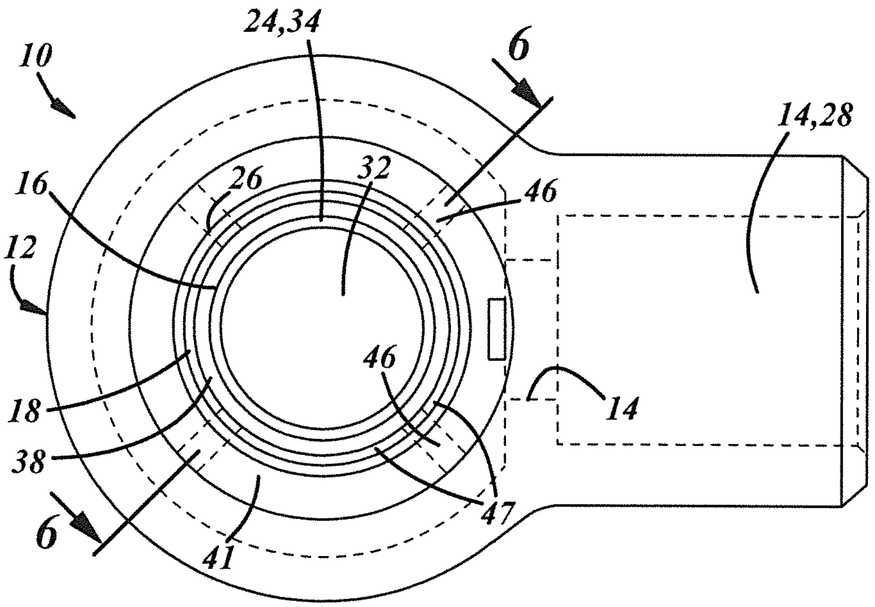
FIG. 3 is a top view of the adhesive applicator device of FIG. 1.

As best shown in FIG. 3, the inner concentric wall 24 of the nozzle 12 may define an axial clearance hole 32 shaped and sized to removably receive a generally rod-shaped nutplate positioning worm 23 shown in FIGS. 2, 4, and 5. The positioning worm 23 may be configured to be received both in the nutplate fastener hole 15 and in a panel fastener hole 25 formed in a panel 27 (shown in FIGS. 7 and 8) to which the nutplate 17 is to be adhered. The positioning worm 23 may include an annular shoulder 29 configured to engage the nutplate 17 and allow an installer to draw and hold the nutplate 17 against the panel 27 with the uncured bead ring 13 sandwiched between, while maintaining the nutplate 17 in concentric alignment with the panel fastener hole 25 as shown in FIG. 7. As shown in FIG. 8, the nutplate positioning worm 23 may be removed once the nutplate 17 has been successfully positioned against and adhered to the panel 27.

When the applicator nozzle 12 is positioned against the nutplate flange 21, as shown in FIG. 5, with the applicator clearance hole 32 positioned concentrically with the nutplate fastener hole 15, a forward end 34 of the inner wall 24 of the applicator device 10 may be seated against the nutplate flange 21 as shown in FIG. 2. Because the inner wall 24 extends axially beyond the outer wall 26, the adhesive material bead ring 13 may be applied, as shown in FIG. 5, while the inner wall 24 blocks the uncured adhesive material 11 from flowing radially inward and prevents the uncured adhesive material 11 from entering and migrating along the nutplate fastener hole 15 between the fastener hole 15 and the worm 23 into locations where, once cured, the adhesive material 11 would limit movement between a floating portion of the nutplate 17 and the nutplate flange 21.

Figure 6:
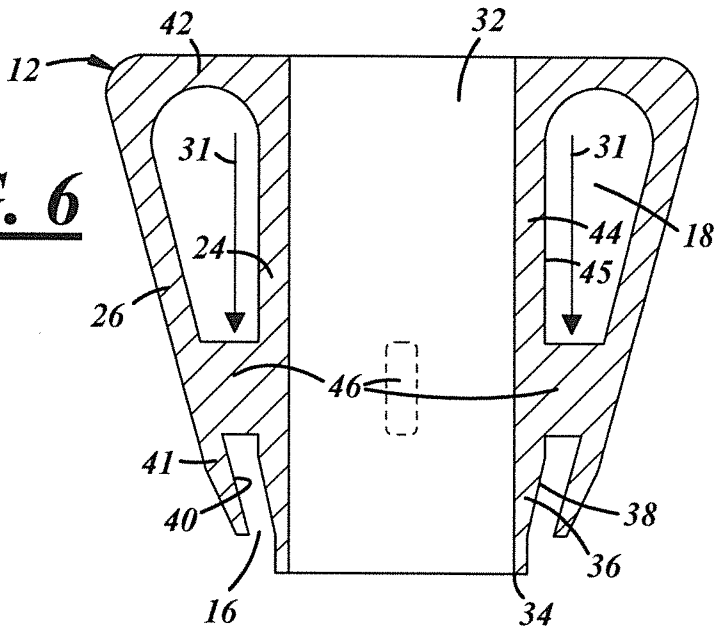
FIG. 6 is a cross-sectional view of the adhesive applicator device of FIG. 3 taken along line 5-5 of FIG. 3.

As best shown in FIGS. 2 and 6, the inner and outer concentric walls 24, 26 of the nozzle 12 may be shaped and positioned such that the nozzle cavity 18, and thus the annular flow path tapers in cross-sectional area in a flow direction 31 of adhesive material 11 along the annular flow path from an upper portion of the nozzle 12 to a lower portion of the nozzle 12. In other words, an axially lower portion 36 of the inner wall 24 may have an inverted frusto-conical radially outwardly-facing surface 38, and the outer wall 26 may have an inverted frusto-conical radially inwardly-facing surface 40 angled and positioned such that a lower portion 41 of the outer wall 26 is disposed generally parallel to, radially opposite, and spaced from the radially outer-facing surface 38 of the lower portion 36 of the inner wall 24. The smaller cross-sectional area of the annular flow path between the lower portions 36, 41 of the inner and outer concentric walls 24, 26; relative to the larger cross-sectional area of the annular flow path in the upper portion of the nozzle 12, causes the adhesive material 11 to flow around the nozzle 12 before being forced downward into and through the lower portions 36, 41 of the nozzle 12. The nozzle 12 may also include an annular upper end wall 42 capping the inner and outer concentric walls 24, 26 and an axially upper portion 44 of the inner concentric wall 24, which may extend from a radially inner periphery of the annular upper end wall 42 to an upper end of the axially lower portion 36 of the inner concentric wall 24. The axially upper portion 44 of the inner concentric wall 24 may have a generally cylindrical radially outward-facing surface 45.

As best shown in FIGS. 3 and 6, the nozzle 12 may include four circumferentially spaced stiffening ribs 46 that extend between the inner and outer concentric walls 24, 26. These circumferentially spaced ribs 46 may be integrally formed as a single unitary piece with the inner and outer concentric walls 24, 26 as is best shown in FIG. 6. The ribs 46 help to maintain a consistent adhesive material bead application by resisting radially outward flexing of the outer concentric wall 26 that might otherwise result from high pressure adhesive material flow through the nozzle 12. The ribs 46 may be thin enough to allow adhesive material to flow around them through intercostal spaces 47 defined by the ribs 46 and shown in FIG. 3.

An adhesive application device constructed as described above, guides the application of a carefully metered adhesive material bead on a surface in a circumferentially continuous bead of uniform shape, size, and volume centered around a hole in the surface, while preventing the sealant from contaminating the hole.

This description, rather than describing limitations of an invention, only illustrates an embodiment of the invention recited in the claims. The language of this description is therefore exclusively descriptive and is non-limiting. Obviously, it's possible to modify this invention from what the description teaches. Within the scope of the claims, one may practice the invention other than as described above.

What is claimed is:

1. An adhesive applicator device for applying adhesive material in a bead ring to a surface, the device comprising:

a nozzle comprising a nozzle intake port, a nozzle outlet port, and a nozzle cavity connecting and providing fluid communication between the inlet and outlet ports;

the outlet port having an annular shape configured to form an annular bead of adhesive material on a surface onto which the nozzle dispenses adhesive material;

the nozzle cavity comprising an annular flow path leading to the annular outlet port and shaped to dispense adhesive material through the outlet port axially; and the nozzle comprising inner and outer concentric walls defining the annular flow path therebetween, the inner concentric wall extending axially beyond the outer concentric wall to allow outward radial movement of adhesive material and to block inward radial encroachment of adhesive material.

2. An adhesive applicator device as defined in claim 1 in which the intake port is configured to receive adhesive material from an adhesive dispenser into the annular flow path.

3. An adhesive applicator device as defined in claim 2 in which an intake fitting is carried by the nozzle and is configured to receive a mixing tip of an adhesive dispenser gun and to guide adhesive material from the mixing tip of the dispenser gun into the nozzle cavity through the nozzle intake port.

4. An adhesive applicator device as defined in claim 3 in which the intake fitting is oriented such that uncured adhesive material is received into the nozzle cavity in a radially inward direction generally perpendicular to the annular flow path.

5. An adhesive applicator device as defined in claim 1 in which the inner concentric wall defines an axial clearance hole for removably receiving a nutplate positioning worm.

6. An adhesive applicator device for applying uncured adhesive material in a bead ring to a surface, the device comprising:

a nozzle comprising a nozzle intake port, a nozzle outlet port, and a nozzle cavity connecting and providing fluid communication between the inlet and outlet ports;

the nozzle intake port being configured to receive uncured adhesive material into the nozzle cavity from a source of uncured adhesive material;

the outlet port having an annular shape configured to form an annular bead of adhesive material on a surface onto which the nozzle dispenses adhesive material;

the nozzle cavity comprising an annular flow path leading to the annular outlet port and shaped to dispense the adhesive material through the outlet port axially;

the nozzle including inner and outer concentric walls that at least partially define the annular flow path and that are shaped and positioned such that the annular flow path tapers in cross-sectional area in a flow direction of adhesive material along the annular flow path; and a positioning worm configured to be removably received within an axial clearance hole of the nozzle.

7. An adhesive applicator device as defined in claim 6 in which the nozzle includes an annular upper end wall capping the inner and outer concentric walls.

8. An adhesive applicator device as defined in claim 7 in which:

an axially lower portion of the inner wall has an inverted frusto-conical radially outwardly-facing surface; and the outer wall has an inverted frusto-conical radially inwardly-facing surface angled and positioned such that a lower portion of the outer wall is disposed generally parallel to, radially opposite, and spaced from the radially outer-facing surface of the lower portion of the inner wall.

9. An adhesive applicator device as defined in claim 8 in which an axially upper portion of the inner wall, which extends from a radially inner periphery of the annular upper end wall to an upper end of the axially lower portion of the inner concentric wall, has a generally cylindrical radially outwardly-facing surface.

10. An adhesive applicator device as defined in claim 6 in which the inner wall of the nozzle extends axially beyond the outer wall so that, by engaging a forward end of the inner wall against a nutplate surface surrounding a fastener hole, the inner wall is positioned to block adhesive material from moving radially inward toward the fastener hole during bead application.

11. An adhesive applicator device as defined in claim 6 in which the inner concentric wall defines the axial clearance hole.

12. An adhesive applicator device as defined in claim 6 in which the nozzle further includes a plurality of circumferentially spaced ribs that extend between the inner and outer concentric walls.

13. An adhesive applicator device as defined in claim 12 in which the plurality of circumferentially spaced ribs is integrally formed with the inner and outer concentric walls as a single unitary piece.

14. An adhesive applicator device as defined in claim 6 in which the positioning worm is configured to be removably received within a fastener hole of a nutplate.

15. An adhesive applicator device as defined in claim 14 in which the positioning worm is configured to be removably received within the axial clearance hole and concurrently within the nutplate fastener hole.

16. An adhesive applicator device as defined in claim 6 in which the positioning worm is configured to be removably received within a fastener hole in a panel.

17. An adhesive applicator device as defined in claim 16 in which the positioning worm is configured to be removably received within the panel fastener hole and concurrently within the nutplate fastener hole.

* * * * *